United States Patent
Bru-Magniez et al.

[11] Patent Number: 5,021,443
[45] Date of Patent: Jun. 4, 1991

[54] NOVAL BENZIMIDAZOLE AND AZABENZIMIAZOLE DERIVATIVES WHICH ARE THROMBOXANE RECEPTOR ANTAGONISTS, THEIR METHODS OF PREPARATION AND PHARMACEUTICAL COMPOSITIONS IN WHICH THEY ARE PRESENT

[75] Inventors: Nicole Bru-Magniez, Paris; Eric Nicolai, Caen; Jean-Marie Teulon, La Celle St Cloud, all of France

[73] Assignee: Laboratoires UPSA, France

[21] Appl. No.: 493,880

[22] Filed: Mar. 15, 1990

[30] Foreign Application Priority Data

Feb. 16, 1990 [FR] France .................. 90 01925

[51] Int. Cl.$^5$ .................................... A61K 31/415
[52] U.S. Cl. ..................... 514/394; 548/325; 548/113
[58] Field of Search ............ 548/325, 113; 514/394

Primary Examiner—Mary C. Lee
Assistant Examiner—Joseph K. McKane
Attorney, Agent, or Firm—Marshall & Melhorn

[57] ABSTRACT

The present invention relates to the derivatives of the formula

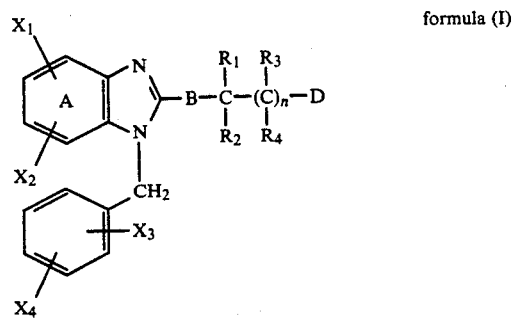

formula (I)

in which:

A is an aromatic ring or a nitrogen heterocycle;

$X_1$, $X_2$, $X_3$ and $X_4$ are independently a hydrogen atom, a halogen atom, a lower alkyl radical, an alkoxy radical, an alkylthio radical, a sulfone group, a sulfoxide group, a trifluoromethyl group, a nitro group, a hydroxyl group, a methylene alcohol radical or a group COOR', in which R' is a hydrogen or a lower alkyl; $X_3$ and $X_4$ can also form a naphthalene with the phenyl;

B is $CR_5R_6$, $R_5$ and $R_6$ being a hydrogen atom or a lower alkyl, or the sulfur atom;

$R_1$, $R_2$, $R_3$ and $R_4$ are independently a hydrogen atom or a lower alkyl radical; $CR_1R_2$ or $CR_3R_4$ can form with B, when the latter is $CR_5R_6$, a cycloalkyl or a cycloalkene having 3 to 7 carbon atoms; $R_1R_2$ and $R_3R_4$ can also form a ring having 3 to 6 carbon atoms;

n is an integer from 1 to 4 and can be 0 if $R_1$ and $R_2$ are other than hydrogen; and D is a chemical group which can be: $COOR_7$, $R_7$ being the hydrogen atom or a lower alkyl, $CONH—R_8$, $R_8$ being the hydrogen atom or a lower alkyl, CN,

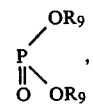

$R_9$ being the hydrogen atom or a lower alkyl, or $NHSO_2CF_3$, and to their addition salts.

13 Claims, No Drawings

NOVAL BENZIMIDAZOLE AND AZABENZIMIAZOLE DERIVATIVES WHICH ARE THROMBOXANE RECEPTOR ANTAGONISTS, THEIR METHODS OF PREPARATION AND PHARMACEUTICAL COMPOSITIONS IN WHICH THEY ARE PRESENT

The present invention relates, by way of novel products, to the benzimidazole and azabenzimidazole derivatives of general formula (I) below and, if appropriate, to their salts.

The compounds in question have a very valuable pharmacological profile insofar as they possess thromboxane receptor antagonist properties. Thromboxane $A_2$ (or $TXA_2$) affects a variety of tissues or cells. A constrictive action is observed on the vascular, bronchial and uterine smooth musculature. The blood platelets are aggregated by $TXA_2$, while the membranes of the circulating cells are modified and can thus adhere to each other. The different properties described for thromboxane $A_2$ are such that a $TXA_2$ receptor antagonist may be envisaged as having a favorable role in the following pathological conditions: myocardial infarction, angina pectoris, stroke, migraine, brain hemorrhage, atherosclerosis, pulmonary embolism, bronchial asthma, bronchitis, pneumonia, circulatory shock of various origins (hemorrhage, septicemia, heart failure, trauma, acute pancreatitis, burn, bacterial origin), nephritis, graft rejection and cancerous metastases.

The present invention further relates to the method of preparing said products and to their applications in therapy. It further relates to the novel intermediates which make it possible to synthesize said products.

These benzimidazole and azabenzimidazole derivatives have general formula (I):

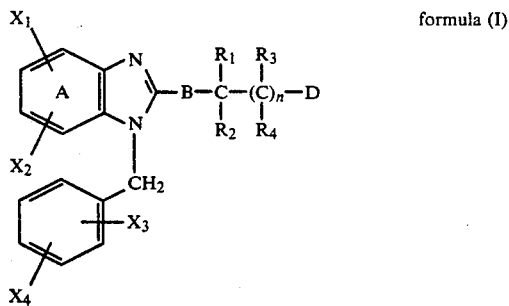

formula (I)

in which:

A is an aromatic ring or a nitrogen heterocycle;

$X_1$, $X_2$, $X_3$ and $X_4$ are independently a hydrogen atom, a halogen atom, a lower alkyl radical, an alkoxy radical, an alkylthio radical, a sulfone group, a sulfoxide group, a trifluoromethyl group, a nitro group, a hydroxyl group, a methylene alcohol radical or a group COOR', in which R' is a hydrogen or a lower alkyl;

$X_3$ and $X_4$ can also form a naphthalene with the phenyl;

B is $CR_5R_6$, $R_5$ and $R_6$ being a hydrogen atom or a lower alkyl, or the sulfur atom;

$R_1$, $R_2$, $R_3$ and $R_4$ are independently a hydrogen atom or a lower alkyl radical; $CR_1R_2$ or $CR_3R_4$ can form with B, when the latter is $CR_5R_6$, a cycloalkyl or a cycloalkene having 3 to 7 carbon atoms; $R_1R_2$ and $R_3R_4$ can also form a ring having 3 to 6 carbon atoms;

n is an integer from 1 to 4 and can be 0 if $R_1$ and $R_2$ are other than hydrogen; and D is a chemical group which can be: $COOR_7$, $R_7$ being the hydrogen atom or a lower alkyl, $CONH-R_8$, $R_8$ being the hydrogen atom or a lower alkyl, CN,

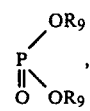

$R_9$ being the hydrogen atom or a lower alkyl, or $NHSO_2CF_3$.

In the description and the claims, lower alkyl is understood as meaning a linear or branched chain having 1 to 6 carbon atoms or a $C_3$-$C_6$ ring, alkoxy is understood as meaning an O-lower alkyl group and alkylthio is understood as meaning an S-lower alkyl group, lower alkyl being as defined above.

In the description and the claims, halogen is understood as meaning a chlorine, bromine, iodine or fluorine atom.

Aromatic ring is understood as meaning any aromatic ring such as benzene or napthalene.

Nitrogen heterocycle is understood as meaning any aromatic ring containing from one to four nitrogens in the ring. Pyridine will be preferred in particular among the nitrogen-containing rings.

The derivatives most similar to these compounds which have so far been disclosed in the literature are described in U.S. Pat. No. 1,580,823 filed in France on Dec. 1, 1967 under U.S. priority of Dec. 2, 1966, No. 598 607, in the name of T. Y. SHEN, A. R. MATZUK and H. SHAM (MERCK and CO.). Said patent describes benzimidazoles substituted in either the 1-position or the 2-position by a lower alkanoic acid residue and in the other position by an aromatic or heteroaromatic group having fewer than three fused rings.

The lower alkanoic acid residue is limited to a chain length of two carbons and can be: —CH$_2$—, —CH$_2$—CH$_2$— or —CH(CH$_3$)—CH$_2$—.

These derivatives are described as antiinflamatories and antipyretics.

The Applicant has found that these compounds are only slightly active, if at all, as thromboxane receptor antagonists.

In fact, the length of the chain which carries the acid group, namely one or two carbon atoms, is insufficient to exhibit a suitable affinity for the receptor.

On the other hand, surprisingly, the Applicant has demonstrated that if this chain possesses more than three carbon atoms or a heteroatom such as sulfur and at least three carbon atoms, and optimally if it is a branched chain having five carbons, the affinity for the receptor is such that it makes it possible to obtain very good $TXA_2$ antagonists.

Variants of the invention form the subject of the sub-claims. In particular, according to these variants, A can be a phenyl ring or a pyridine ring and $X_1$ can be a fluorine atom or a chlorine atom. Likewise, $X_3$ can be a chlorine atom or a methoxy group; D can advantageously be an acid group.

Also according to a particular variant, B can be a methylene group, $R_1$ and $R_2$ are each a methyl, $R_3$ and $R_4$ are hydrogen and n is equal to 1.

According to another advantageous variant, B is the sulfur atom.

According to yet another variant, C and $R_1$ and $R_2$ are a cyclopentane.

The particularly preferred compounds of the invention are those selected from the products of the formulae.

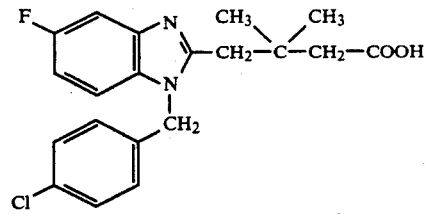

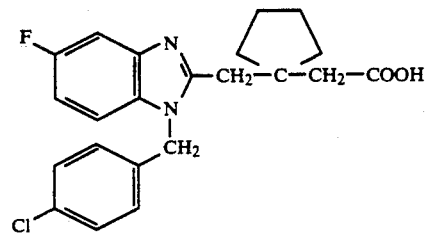

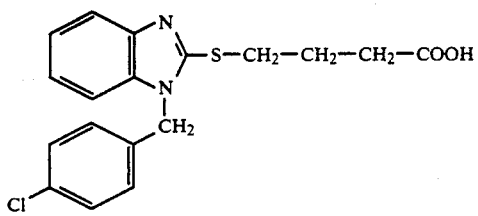

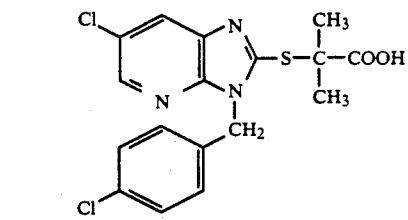

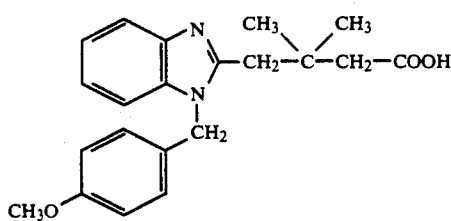

A - Method of preparing the compounds of formula (I) in which B is the sulfur atom According to the invention, the compounds of formula (I) in which B is the sulfur atom and D is a group $COOR_7$, A, $X_1$, $X_2$, $X_3$, $X_4$, $R_1$, $R_2$, $R_3$, $R_4$ and n being as defined above and $R_7$ being a lower alkyl group, can be synthesized by reacting an alkyl halogenoalkanoate of formula (II):

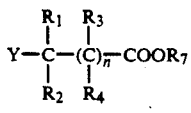

formula (II)

in which $R_1$, $R_2$, $R_3$, $R_4$, n and $R_7$ are as defined above and Y is a halogen, optimally chlorine or bromine, with a mercaptobenzimidazole or mercaptoazabenzimidazole derivative of formula (III):

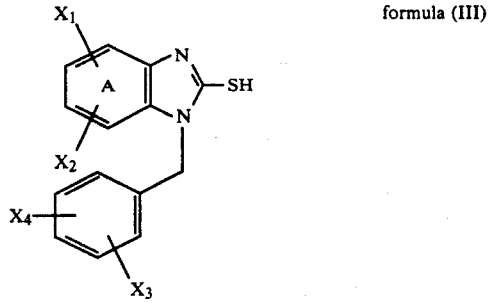

formula (III)

in which A, $X_1$, $X_2$, $X_3$ and $X_4$ are as defined above, in the presence of a base such as a sodium or potassium alcoholate in an alcohol, sodium hydride in dimethylformamide or potassium carbonate in acetone or butan-2-one.

The compounds of formula (III) are synthesized by reacting carbon disulfide or potassium xanthogenate with diamine compounds of formula (IV):

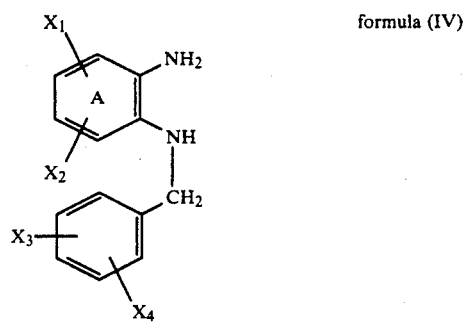

formula (IV)

in which A, $X_1$, $X_2$, $X_3$ and $X_4$ are as defined above, under reflux in a solvent such as an alcohol.

The compounds of formula (IV) can be obtained by catalytic hydrogenation of the nitro derivatives of formula (V):

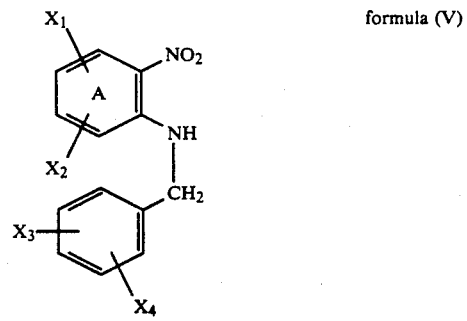

formula (V)

in which A, $X_1$, $X_2$, $X_3$ and $X_4$ are as defined above, in the presence of Raney nickel for example, in solvents such as an alcohol, tetrahydrofuran or 2-methoxyethanol, under pressure or at atmospheric pressure and at a temperature of between 20° and 120° C.

These nitro derivatives of formula (V) can be synthesized by reacting a substituted benzylamine of formula (VI):

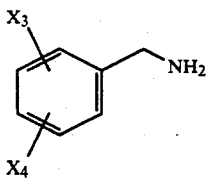

formula (VI)

in which $X_3$ and $X_4$ are as defined above, with a halogenated nitro derivative of formula (VII):

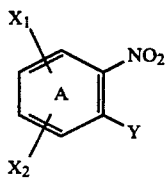

formula (VII)

in which A, $X_1$ and $X_2$ are as defined above and Y is a halogen atom, optimally chlorine or fluorine.

In the case where A is a phenyl, the reaction can be carried out in a solvent such as an alcohol or tetrahydrofuran, in the presence of potassium carbonate, or simply by heating the reactants at 135° C., without a solvent or a base, according to the method described in Belgian patent No. 667,333 of Jan. 24, 1966.

In the case where A is a nitrogen hetercycle, for example pyridine or pyrimidine, the reaction may be carried out in solvents such as toluene or xylene, in the presence or absence of pyridine or 2-methyl-5-ethylpyridine.

The benzylamines of formula (VI) are commercially available or can be prepared by:
hydrogenation of the corresponding Schiff base obtained by reacting ammonia with the corresponding aldehyde under pressure;
hydrogenation of the corresponding oxime obtained by reacting hydroxylamine with the corresponding aldehyde; or
Hofmann degradation of the corresponding phenylacetamide, i.e. treatment with a solution of a hypohalite, for example sodium hypobromite.

The orthohalogenated nitro derivatives of formula (VII) are commercially available or can be synthesized according to methods described in the literature, for example in the following references: in the case where A is a phenyl:
HOLLEMAN; REIDING; Rec. Trav. Chim. Pays Bas 1904, 23, 361
SWARTS; Rec. Trav. Chim. Pays Bas 1916, 35, 155 in the case where A is a nitrogen heterocycle:
BATKOWSKI, T.; Rocz. Chem. 1968, 42 (12), 2079–88

BEBENBURG, W.; STEIMMETZ, S.; THIELE, K.; Chemische Zeitung 1979, 103 (12), 387–99
BOON, W. R.; JONES, W. G. M.; RAMAGE, G. R.; J. Chem. Soc. 1951, 96
KRUGER, S.; MANN, F. G.; J. Chem. Soc. 1955, 2755
FUJIMATO, M.; Pharm. Bull. (Tokyo) 1956, 4, 340

The nitro compounds of formula (V) in which A is a phenyl can also be prepared in several steps from nitroanilines of formula (VII) in which A is a phenyl and Y=NH$_2$. In a first stage, these nitroanilines are treated with tosyl chloride in pyridine. The resulting sulfonamide is then alkylated with an appropriately substituted benzyl chloride in the presence of a metalating agent such as sodium hydride, in a solvent such as dimethylformamide. The tosylate (4-methylbenzenesulfonyl) group is then hydrolyzed in propionic acid, in the presence of concentrated sulfuric acid, to give the corresponding nitro derivatives of formula (V).

B - Method of preparing the compounds of formula (I) in which B is a group $CR_5R_6$ The derivatives of formula (I) in which B is a group $CR_5R_6$ and D is a group $COOR_7$, A, $X_1$, $X_2$, $X_3$, $X_4$, $R_1$, $R_2$, $R_3$, $R_4$, $R_5$, $R_6$ and n being as defined above and $R_7$ being a lower alkyl group, can be synthesized by reacting derivatives of formula (IV) with derivatives of formula (VIII):

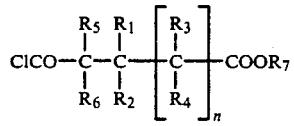

formula (VIII)

in which $R_1$, $R_2$, $R_3$, $R_4$, $R_5$, $R_6$ and n are as defined above and $R_7$ is a lower alkyl.

These derivatives of formula (VIII) can be prepared, according to a classical method of forming acid chlorides, by treating the corresponding acid ester derivatives of formula (IX):

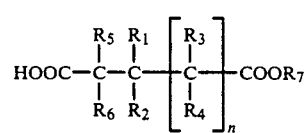

formula (IX)

in which $R_1$, $R_2$, $R_3$, $R_4$, $R_5$, $R_6$ and n are as defined above and $R_7$ is a lower alkyl, with thionyl chloride or phosphorus oxychloride for example, in a solvent such as toluene for example, or without a solvent.

These compounds of formula (IX) are obtained by different routes:
by monosaponification of the corresponding diesters in the presence of one equivalent of sodium hydroxide, according to a procedure described for example in the following reference: LE MOAL H.; FOUCAUD A.; CARRIE R.; DANION D. and FAYAT C.; Bull. Soc. Chim. Fr. 1964, 828
by treatment of the corresponding acid anhydride derivatives with an alcohol, these acid anhydrides being obtained by dehydration of the corresponding diacids with acetic anhydride under reflux, or by treatment with half an equivalent of dicyclohexylcarbodiimide; the preparation of the diacid derivatives used which are not commercially available may be found in the following references:
HOWARD E. ZIMMERMAN; DAVID N. SCHISSEL; J. Org. Chem. 1986, 51, 196–207
H. NAJER; R. GIUDICELLI; J. SETTE; Bull. Soc. Chim. Fr. 1964, 2572–2581
J. SEYDEN PENNE; M. C. ROUX-SCHMITT; Bull. Soc. Chim. Fr. 1968, 3812
N. L. ALLINGER; M. NAKAZAKI; V. ZALKOW; J. Am. Chem. Soc. 1959, 81, 4074–4080
J. MEINWALD; J. J. TUFARIELLO; J. J. HURST; J. Am. Chem. Soc. 1964, 86, 2914–2920

This reaction between the acid chloride esters of formula (VIII) and the diamino derivatives of formula (IV) is performed in two steps.

In a first stage, in a solvent such as chloroform or tetrahydrofuran for example, in the presence of triethylamine or pyridine, it yields a mixture of amide compounds of formulae (X) and (X bis):

formula (X)

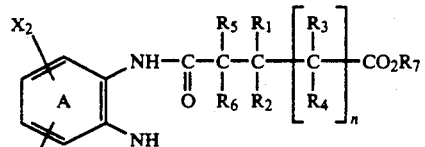

formula (X bis)

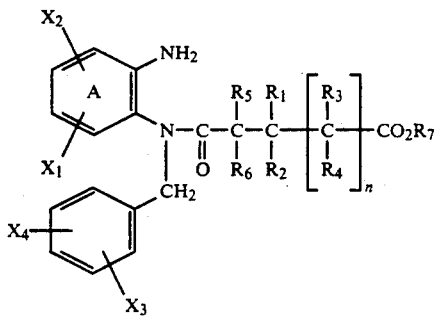

in which A, X₁, X₂, X₃, X₄, R₁, R₂, R₃, R₄, R₅, R₆ and n are as defined above and R₇ is a lower alkyl.

This mixture of amide compounds of formulae (X) and (X bis) is then treated in an acid medium, either with concentrated hydrochloric acid in an alcohol under reflux, or with concentrated sulfuric acid, or with polyphosphoric acid, to give the compounds of formula (I) in which B is a group CR₅R₆ and D is a group CO₂R₇, R₇ being a lower alkyl.

The compounds of formula (I) in which A is a phenyl and D is the group CO₂R₇, R₇ being a lower alkyl, can also be synthesized by reacting an appropriately substituted benzyl chloride with derivatives of formula formula (XI)

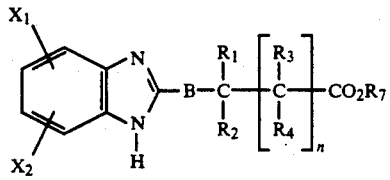

in which X₁, X₂, R₁, R₂, R₃, R₄, B and n are as defined above and R₇ is a lower alkyl, in a solvent such as dimethylformamide, in the presence of a metalating agent such as sodium hydride.

The compounds of formula (XI) in which B is the sulfur atom can be synthesized from the compounds of formula (XII):

formula (XII)

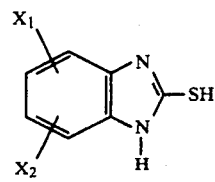

in which X₁ and X₂ are as defined above, with alkyl halogenoalkanoate compounds of formula (II) in the presence of a base such as sodium ethylate in alcohol or potassium carbonate in acetone or tetrahydrofuran.

The compounds of formula (XII) are commercially available or are synthesized according to methods described in BEILSTEIN 24, 119 and 24, supplement (3), 293.

The compounds of formula (XI) in which B is a group CR₅R₆, R₅ and R₆ being as defined above, can be synthesized by reacting an acid chloride ester compound of formula (VIII) with an orthophenylenediamine compound of formula (XIII):

formula (XIII)

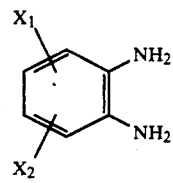

in which X₁ and X₂ are as defined above, under conditions identical to those described above for reacting the compounds of formula (IV) with the derivatives of formula (VIII).

The compounds of formula (XIII) are commercially available.

The compounds of formula (I) in which D is the group COOR₇ and R₇ is the hydrogen atom are obtained by classical hydrolysis of the compounds of formula (I) in which D is the group COOR₇ and R₇ is a lower alkyl, either in an acid medium or in a basic medium.

The compounds of formula (I) in which D is a group CONH-R₈ are obtained by reacting amines of the formula R₈-NH₂, R₈ being as defined above, with acid chlorides of formula (XIV):

formula (XIV)

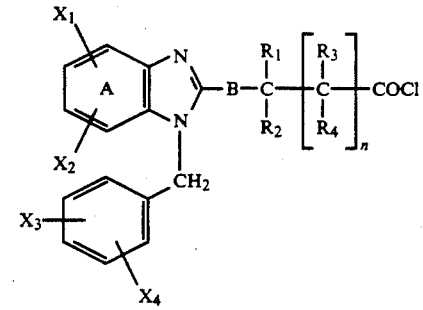

in which A, X₁, X₂, X₃, X₄, R₁, R₂, R₃, R₄, B and n are as defined above, in a solvent such as chloroform or tetrahydrofuran, in the presence of excess amine or of triethylamine or pyridine. In the case where R₈ is hydrogen, it will be possible quite simply to react the acid chloride of formula (XIV) with a solution of ammonia.

The compounds of formula (XIV) can be prepared according to a classical method for acid chlorides, namely by reacting thionyl chloride, oxalyl chloride or phosphorus oxychloride with the corresponding compounds of formula (I) in which D is the group $CO_2H$.

The compounds of formula (I) in which D is the group CN can be prepared by dehydration of the corresponding amide compounds, in which D is $CONH_2$, by treatment with phosphorus oxychloride for example, in a solvent such as dimethylformamide or without a solvent.

The compounds of formula (I) in which D is the group $-PO(OR_9)_2$, $R_9$ being a lower alkyl, can be obtained by reacting a trialkyl phosphite $P(OR_9)_3$ with a halogenated compound of formula (XV):

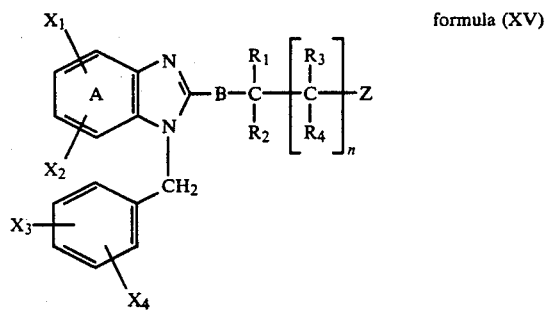

formula (XV)

in which A, B, $X_1$, $X_2$, $X_3$, $X_4$, $R_1$, $R_2$, $R_3$, $R_4$ and n are as defined above and Z is a halogen, optimally chlorine or bromine, by heating, the trialkyl phosphite being used as the solvent.

In the case where n is other than 0 and $R_3$ and $R_4$ are hydrogen atoms, the derivatives of formula (XV) can be obtained by chlorination of the corresponding alcohols with thionyl chloride or bromination with phosphorus tribromide, said alcohols themselves being obtained by reduction of the acids or esters of formula (I) in which D is $COOR_7$, $R_7$ being the hydrogen atom or a lower alkyl, with reducing agents such as lithium aluminum hydride or sodium or lithium borohydride, in an appropriate solvent such as ethyl ether, tetrahydrofuran or dioxane.

The derivatives of formula (XV) in which B is the group $CR_5R_6$, $CR_3R_4$ and n being as defined in formula (I), can be synthesized by reacting derivatives of formula (XVI):

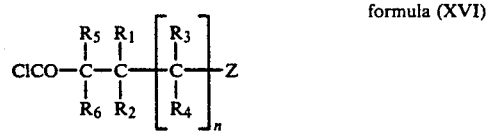

formula (XVI)

in which $R_1$, $R_2$, $R_3$, $R_4$, $R_5$, $R_6$, n and Z are as defined above, with compounds of formula (IV) under the conditions described for reacting the compounds of formula (VIII) with those of formula (IV) to give the compounds of formula (I) in two steps.

The compounds of formula (XV) in which B is the sulfur atom, $CR_3R_4$ and n being as defined in formula (I), can be prepared by chlorination or bromination of the corresponding alcohols according to the methods indicated above, said alcohols being prepared by reacting a halogeno alcohol of formula (XVII):

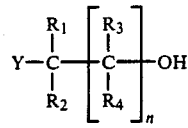

formula (XVII)

in which $R_1$, $R_2$, $R_3$, $R_4$ and n are as defined above, Y being a halogen atom, optimally chlorine or bromine, with derivatives of formula (III) in the presence of a base such as sodium ethylate or potassium carbonate, in a solvent such as an alcohol, acetone or butan-2-one.

The compounds of formula (I) in which D is the group $PO(OH)_2$ can be obtained from the compounds of formula (I) in which D is the group $PO(OR_9)_2$, $R_9$ being a lower alkyl, by hydrolysis in 36% hydrochloric acid under reflux.

The derivatives of formula (I) in which D is the group $NHSO_2CF_3$ can be obtained by reacting trifluoromethanesulfonyl chloride with derivatives of formula (XVIII):

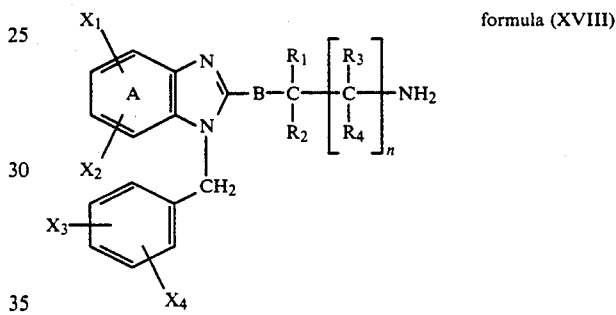

formula (XVIII)

in which A, $X_1$, $X_2$, $X_3$, $X_4$, B, $R_1$, $R_2$, $R_3$, $R_4$ and n are as defined above, in the presence of a base such as triethylamine or pyridine, in a solvent such as chloroform, tetrahydrofuran or toluene.

These amino compounds of formula (XVIII) can be obtained by Hofmann degradation, for example treatment with a solution of sodium hypobromite, of the corresponding amide derivatives of formula (I) in which D is the group $-CONH_2$, the preparation of which has been mentioned above.

Addition salts of some of the compounds of formula (I) can be obtained, especially pharmaceutically acceptable addition salts. The sodium, potassium and calcium salts may be mentioned in particular when D is an acid group.

The novel compounds according to the invention possess remarkable pharmacological properties as thromboxane receptor antagonists and can be used in therapy for the treatment of myocardial infarction, angina pectoris, stroke, migraine, cerebral hemorrhages, atherosclerosis, pulmonary embolism, bronchial asthma, bronchitis, pneumonia, circulatory shocks of various origins, nephritis, graft rejection and cancerous metastases.

Thus the invention also covers a pharmaceutical composition which comprises a pharmaceutically effective amount of at least one compound of formula (I) as defined above, as well as its pharmaceutically acceptable addition salts if appropriate, which may or may not be incorporated in a pharmaceutically acceptable excipient, vehicle or carrier.

The invention also covers a pharmaceutical composition active as a thromboxane receptor antagonist, with which the following diseases in particular can be favorably treated: myocardial infarction, angina pectoris, stroke, migraine, cerebral hemorrhage, atherosclerosis, pulmonary embolism, bronchial asthma, bronchitis, pneumonia, circulatory shocks of various origins such as hemorrhage, septicemia, heart failure, trauma, acute pancreatitis, burn or bacterial origin, nephritis, graft rejection and cancerous metastases, said composition comprising a pharmaceutically effective amount of at least one compound of formula (I) mentioned above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a therapeutically effective amount of at least one compound of formula (I) as defined above, as well as its pharmaceutically acceptable addition salts if appropriate, into a pharmaceutically acceptable excipient, vehicle or carrier. In another embodiment, a pharmaceutical composition active as a thromboxane receptor antagonist is prepared with which the following diseases in particular can be favorably treated: myocardial infarction, angina pectoris, stroke, migraine, cerebral hemorrhage, atherosclerosis, pulmonary embolism, bronchial asthma, bronchitis, pneumonia, circulatory shocks of various origins such as hemorrhage, septicemia, heart failure, trauma, acute pancreatitis, burn or bacterial origin, nephritis, graft rejection and cancerous metastases.

In another variant, a pharmaceutical composition is prepared in the form of gelatin capsules or tablets containing from 1 to 200 mg of active ingredient, or in the form of injectable preparations containing from 0.01 to 10 mg of active ingredient.

The invention also covers a method of therapeutic treatment for mammals, which comprises administering to said mammal a therapeutically effective amount of at least one compound of formula (I) as defined above, or one of its pharmaceutically acceptable addition salts, which may or may not be incorporated in a pharmaceutically acceptable excipient, vehicle or carrier. In a variant of this method of treatment, the compound of formula (I), either by itself or in association with a pharmaceutically acceptable excipient, is prepared in the form of gelatin capsules or tablets containing from 1 to 200 mg of active ingredient for oral administration, or in the form of injectable preparations containing from 0.01 to 10 mg of active ingredient for parenteral administration.

In human and animal therapy, the compounds of formula (I) and their salts can be administered, by themselves or in association with a physiologically acceptable excipient, in any form, in particular in the form of gelatin capsules and tablets for oral administration or in the form of an injectable solution for parenteral administration.

As will become clearly apparent from the pharmacology tests given at the end of the description, the compounds according to the invention can be administered in human therapy, for the abovementioned indications, orally in the form of tablets or gelatin capsules containing from 1 to 200 mg of active ingredient, or parenterally in the form of injectable preparations containing from 0.01 to 10 mg of active ingredient, in one or more dosage units per day for an adult with an average weight of 60 to 70 kg.

In animal therapy, the daily dose which can be used should normally be between 1 and 100 mg per kg.

Further characteristics and advantages of the invention will be understood more clearly from the following description of some Preparatory Examples, which in no way imply a limitation but are given by way of illustration.

EXAMPLE 1

2-(4-Chlorophenylmethylamino)-5-fluoronitrobenzene

Formula (V): $X_1=5\text{-F}$, $X_2=X_3=H$, $X_4=4\text{-Cl}$, $A=$ phenyl 30 g of 2,5-difluoronitrobenzene and 26.7 g of 4-chlorobenzylamine are dissolved in 300 ml of tetrahydrofuran. 40 g of potassium carbonate are added to this solution and the mixture is refluxed for 8 hours. After cooling, the reaction mixture is added to 1.7 l of water and 50 ml of concentrated hydrochloric acid. The crystals obtained are filtered off and washed with water and then with isopropyl ether to give 41.9 g of 2-(4-chlorophenylmethylamino)-5-fluoronitrobenzene in the form of crystals melting at 160° C.

The following Example was synthesized by this procedure:

EXAMPLE 2

2-(3,4-Dichlorophenylmethylamino)-5-fluoronitrobenzene

Formula (V): $X_1=5\text{-F}$, $X_2=H$, $X_3=3\text{-Cl}$, $X_4=4\text{-Cl}$, $A=$phenyl Crystals melting at 110° C.

EXAMPLE 3

2-(4-Chlorophenylmethylamino)-5-chloronitrobenzene

Formula (V): $X_1=5\text{-Cl}$, $X_2=H$, $X_3=4\text{-Cl}$, $X_4=H$, $A=$phenyl 25 g of 2,5-dichloronitrobenzene and 36.9 g of 4-chlorobenzylamine are heated for two hours at 135° C., it being necessary for the temperature always to be kept below 140° C. After cooling, the mixture is taken up with water and extracted with ethyl acetate. After drying over magnesium sulfate and evaporation under vacuum, the residue is taken up with ether and the crystals obtained are filtered off and washed with ether to give 22.3 g of 2-(4-chlorophenylmethylamino)-5-chloronitrobenzene in the form of crystals melting at 120° C.

EXAMPLE 4

2-(4-Chlorophenylmethylamino)-5-methoxynitrobenzene

Formula (V): $X_1=5\text{-OMe}$, $X_2=H$, $X_3=4\text{-Cl}$, $X_4=H$, $A=$phenyl (A) 2-(4-Methylbenzenesulfonylamino)-5-methoxynitrobenzene 50 g of 4-methoxy-2-nitroaniline are stirred at 0° C. in 300 ml of pyridine. 56.7 g of tosyl chloride are added in portions at 0° C. and the mixture is then stirred for two hours at room temperature, left to stand overnight and poured into an ice/water mixture. The crystals obtained are filtered off and washed with water and then with isopropyl ether to give 72.8 g of 2-(4-methylbenzenesulfonylamino)-5-methoxynitrobenzene in the form of crystals melting at 99° C.

(B) N-(4-Chlorobenzyl)-N-(4-methylbenzenesulfonyl)-2-nitro-4-methoxyaniline 72.8 g of 2-(4-methylbenzenesulfonylamino)-5-methoxynitrobenzene, prepared in (A), are added to 56.5 ml of 4N sodium hydroxide solution and 29.2 g of 4-chlorobenzyl chloride. The mixture is refluxed for 4 hours, a further 43.7 g of 4-chlorobenzyl chloride are then added and the resulting mixture is refluxed for another 45 minutes. After cooling, 12.2 ml of 35% sodium hydroxide solution are added to the reaction mixture, the latter is refluxed for three hours 45 minutes and then cooled and water and ether are added. The insoluble material is filtered off and washed with water and ether to give 98 g of N-(4-chlorobenzyl)-N-(4-methylbenzenesulfonyl)-2-nitro-4-methoxyaniline in the form of crystals melting at 124° C. Evaporation of the ether phase yields an additional 10 g of crystals melting at 124° C.

(C) 2-(4-Chlorophenylmethylamino)-5-methoxynitrobenzene 108 g of N-(4-chlorobenzyl)-N-(4-methylbenzenesulfonyl)-2-nitro-4-methoxyaniline, prepared in (B), are added to 940 ml of propionic acid and 102 ml of concentrated sulfuric acid. The mixture is heated at 95° C. for 1 h 30 min and the solution is concentrated to half its volume by evaporation under vacuum and then poured on to ice and neutralized with ammonium hydroxide. The crystals obtained are filtered off and washed with water and then with isopropyl ether to give 60 g of 2-(4-chlorophenylmethylamino)-5-methoxynitrobenzene in the form of crystals melting at 135° C.

EXAMPLE 5

2-(4-Chlorophenylmethylamino)-3-nitropyridine

Formula (V): $X_3=4$-Cl, $X_1=X_2=X_4=H$, $A=$pyridin-2-yl

A solution of 26.5 g of 2-chloro-3-nitropyridine, 23.7 g of 4-chlorobenzylamine and 25 ml of 2-methyl-5-ethylpyridine in 200 ml of xylene is refluxed for 12 hours. The reaction mixture is then cooled, water and acetic acid are added and the resulting mixture is then extracted with ether. The organic phase is dried over magnesium sulfate, filtered and then evaporated under vacuum to give an oil which crystallizes from isopropyl ether. The crystals are filtered off and then dried to give 27 g of 2-(4-chlorophenylmethylamino)-3-nitropyridine in the form of crystals melting at 100° C.

EXAMPLE 6

2-(4-Chlorophenylmethylamino)-3-nitro-5-chloropyridine

Formula (V): $X_1=5$-Cl, $X_2=H$, $X_3=4$-Cl, $X_4=H$, $A=$pyridin-2-yl

A solution of 20.9 g of 4-chlorobenzylamine and 15.7 g of 2,5-dichloro-3-nitropyridine in 250 ml of xylene and 20 ml of 2-methyl-5-ethylpyridine is refluxed for 30 hours. After cooling, water is added to the reaction mixture, the resulting mixture is then extracted with ethyl acetate and the organic phase is washed with a dilute solution of hydrochloric acid and dried over magnesium sulfate. The solvent is evaporated off under vacuum and the residue obtained crystallizes from isopropyl ether to give 21.1 g of 2-(4-chlorophenylmethylamino)-3-nitro-5-chloropyridine in the form of crystals melting at 120° C.

EXAMPLE 7

2-(2-Fluoro-4-bromophenylmethylamino)-3-nitro-5-chloropyridine

Formula (V): $X_1=5$-Cl, $X_2=H$, $X_3=2$-F, $X_4=4$-Br, $A=$pyridin-2-yl

Prepared by the procedure of Example 6.
Crystals melting at 75°–77° C.

EXAMPLE 8

2-(4-Chlorophenylmethylamino)-5-fluoroaniline

Formula (IV): $X_1=5$-F, $X_2=H$, $X_3=4$-Cl, $X_4=H$, $A=$phenyl 41.7 g of 2-(4-chlorophenylmethylamino)-5-fluoronitrobenzene, prepared in Example 1, are dissolved in 1 l of tetrahydrofuran and hydrogenated at ordinary temperature and pressure in the presence of 5 g of Raney nickel. When the theoretical amount of hydrogen has been absorbed, the catalyst is filtered off and the solvent is evaporated off under vacuum to give 34.1 g of 2-(4-chlorophenylmethylamino)-5-fluoroaniline in the form of crystals melting at 99° C.

The following Examples were prepared by the same procedure:

EXAMPLE 9

2-(4-Chlorophenylmethylamino)-5-methoxyaniline

Formula (IV): $X_1=5$-MeO, $X_2=H$, $X_3=4$-Cl, $X_4=H$, $A=$phenyl

Crystals melting at 90° C.

EXAMPLE 10

2-(3,4-Dichlorophenylmethylamino)-5-fluoroaniline

Formula (IV): $X_1=5$-F, $X_2=H$, $X_3=3$-Cl, $X_4=4$-Cl, $A=$phenyl

Crystals melting at 104° C.

EXAMPLE 11

2-(4-Chlorophenylmethylamino)-5-chloroaniline

Formula (IV): $X_1=5$-Cl, $X_2=H$, $X_3=4$-Cl, $X_4=H$, $A=$phenyl

Crystals melting at 138° C.

EXAMPLE 12

2-(2-Fluoro-4-bromophenylmethylamino)-3-amino-5-chloropyridine

Formula (IV): $X_1=5$-Cl, $X_2=H$, $X_3=2$-F, $X_4=4$-Br, $A=$pyridin-2-yl

Crystals melting at 97° C.

EXAMPLE 13

2-(4-Chlorophenylmethylamino)-3-aminopyridine

Formula (IV): $X_1=H$, $X_2=H$, $X_3=4$-Cl, $X_4=H$, $A=$pyridin-2-yl

Crystals melting at 132° C.

EXAMPLE 14

2-(4-Chlorophenylmethylamino)-3-amino-5-chloropyridine

Formula (IV): $X_1=H$, $X_2=H$, $X_3=4$-Cl, $X_4=H$, $A=$pyridin-2-yl

Oil used as such for the next step.

EXAMPLE 15

1-(4-Chlorophenylmethyl)-2-mercapto-5-fluorobenzimidazole

Formula (III): $X_1=5$-F, $X_2=H$, $X_3=4$-Cl, $X_4=H$, A=phenyl 25 ml of carbon disulfide are added to 35.2 g of 2-(4-chlorophenylmethylamino)-5-fluoroaniline, prepared in Example 8, dissolved in 500 ml of ethanol. The mixture is refluxed for 12 hours and allowed to return to room temperature. After standing for a few hours, the crystals are filtered off and washed with ethanol and then with isopropanol and ether to give 33 g of 1-(4-chlorophenylmethyl)-2-mercapto-5-fluorobenzimidazole in the form of crystals melting at 215° C.

The following Examples were prepared by the same procedure:

EXAMPLE 16

1-(4-Chlorophenylmethyl)-2-mercaptoimidazo[4,5-b]pyridine

Formula (III): $X_3=4$-Cl, $X_1=X_2=X_4=H$, A=pyridin-2-yl

Crystals melting at 216° C.

EXAMPLE 17

1-(4-Chlorophenylmethyl)-2-mercapto-5-chloroimidazo[4,5-b]pyridine

Formula (III): $X_1=5$-Cl, $X_2=H$, $X_3=4$-Cl, $X_4=H$, A=pyridin-2-yl

Crystals melting at 260° C.

EXAMPLE 18

1-(2-Fluoro-4-bromophenylmethyl)-2-mercapto-5-chloropyridine

Formula (III): $X_1=5$-Cl, $X_2=H$, $X_3=2$-F, $X_4=4$-Br, A=pyridin-2-yl

Crystals melting at 240° C.

EXAMPLE 19

Ethyl 4-[1-(4-chlorobenzyl)-5-fluorobenzimidazol-2-yl]-mercaptobutanoate

Formula (I): $X_1=5$-F, $X_2=H$, $X_3=4$-Cl, $X_4=H$, A=phenyl, B=S, D=$CO_2Et$, $R_1=R_2=R_3=R_4=H$, n=2

9 g of 1-(4-chlorophenylmethyl)-2-mercapto-5-fluorobenzimidazole, prepared in Example 15, and 4.4 ml of ethyl 4-bromobutyrate are refluxed for 5 hours in 100 ml of acetone in the presence of 6.3 g of potassium carbonate. The solvent is evaporated off under vacuum, the residue is taken up in water and then extracted with ethyl acetate and the extract is washed with a dilute solution of sodium hydroxide. The organic phase is dried over magnesium sulfate and evaporated under vacuum to give 11.9 g of ethyl 4-[1-(4-chlorobenzyl)-5-fluorobenzimidazol-2-yl]mercaptobutanoate in the form of an oil, which is used as such for the next step.

The following Examples were prepared by the same procedure:

EXAMPLE 20

Ethyl 5-[1-(4-chlorobenzyl)-5-fluorobenzimidazol-2-yl]-mercaptopentanoate

Formula (I): $X_1=5$-F, $X_2=H$, $X_3=4$-Cl, $X_4=H$, A=phenyl, B=S, D=$CO_2Et$, $R_1=R_2=R_3=R_4=H$, n=3

Oil used as such for the next step.

EXAMPLE 21

Ethyl 4-[1-(2-fluoro-4-bromobenzyl)-5-chloroimidazo[4,5-b]pyridin-2-yl]mercaptobutanoate Formula (I): $X_1=5$-Cl, $X_2=H$, $X_3=2$-F, $X_4=4$-Br, A=pyridin-2-yl, D=$CO_2Et$, B=S, $R_1=R_2=R_3=R_4=H$, n=2

Crystals melting at 94° C.

EXAMPLE 22

Ethyl 2-[1-(4-chlorobenzyl)-5-chloroimidazo[4,5-b]-pyridin-2-yl]mercapto-2-methylpropionate Formula (I): $X_1=5$-Cl, $X_2=H$, $X_3=4$-Cl, $X_4=H$, A=pyridin-2-yl, D=$CO_2Et$, B=S, $R_1=R_2=R_3=CH_3$, n=0

Oil used as such for the next step.

EXAMPLE 23

Ethyl 4-[1-(4-chlorobenzyl)imidazo[4,5-b]pyridin-2-yl]-mercaptobutanoate

Formula (I): $X_1=H$, $X_2=X_3=H$, $X_4=4$-Cl, A=pyridin-2-yl, D=$CO_2Et$, B=S, $R_1=R_2=R_3=R_4=H$, n=2

Oil used as such for the next step.

EXAMPLE 24

Ethyl 4-(benzimidazol-2-yl)mercaptobutanoate

Formula (XI): $X_1=X_2=H$, B=S, $R_7=Et$, $R_1=R_2=R_3=R_4=H$, n=2

50 g of 2-mercaptobenzimidazole are dissolved in 300 ml of ethanol, and a solution of 7.65 g of sodium in 150 ml of ethanol is added at room temperature, with stirring. The mixture is stirred for a few minutes at room temperature and 64.3 g of ethyl 4-bromobutyrate are added rapidly. The reaction mixture is refluxed for 6 hours and then cooled. The solvents are evaporated off to dryness under vacuum, the residue is taken up with water and the crystals obtained are filtered off, washed with water and then with ether and dried to give 85 g of ethyl 4-(benzimidazol-2-yl)mercaptobutanoate in the form of crystals melting at 70°-72° C.

EXAMPLE 25

Ethyl 5-(benzimidazol-2-yl)mercaptopentanoate

Formula (XI): $X_1=X_2=H$, B=S, $R_7=Et$, $R_1=R_2=R_3=R_4=H$, n=3

Prepared by the procedure of Example 24.

Crystals melting at 100° C.

EXAMPLE 26

Ethyl 4-[1-(4-chlorobenzyl)benzimidazol-2-yl]mercaptobutanoate

Formula (I): $X_1=H$, $X_2=X_3=H$, $X_4=4\text{-Cl}$, A=phenyl, $D=CO_2Et$, B=S, $R_1=R_2=R_3=R_4=H$, n=2

20 g of ethyl 4-(benzimidazol-2-yl)mercaptobutanoate, prepared in Example 24, are added to a suspension of 2.9 g of 60% sodium hydride in 150 ml of anhydrous dimethylformamide. The mixture is stirred for 30 minutes at 80° C. and then cooled to room temperature and a solution of 12.7 g of 4-chloro-chloromethylbenzene in 20 ml of anhydrous dimethylformamide is added dropwise. The mixture is refluxed for 5 hours and the solvent is evaporated off to dryness. The residue is taken up with water and extracted with ethyl acetate and the organic phase is dried and then evaporated under vacuum to give 27 g of ethyl 4-[1-(4-chlorobenzyl)benzimidazol-2-yl]-mercaptobutanoate in the form of an oil, which is used as such for the next step.

The following Example was prepared by the same procedure:

EXAMPLE 27

Ethyl 4-[1-(2,4-dichlorobenzyl)imidazol-2-yl]mercaptobutanoate

Formula (I): $X_1=H$, $X_2=H$, $X_3=2\text{-Cl}$, $X_4=4\text{-Cl}$, A=phenyl, $D=CO_2Et$, B=S, $R_1=R_2=R_3=R_4=H$, n=2

Crystals melting at 92° C.

EXAMPLE 28

Acid chloride ethyl ester of 3,3-dimethylglutaric acid

Formula (VIII): $R_5=R_6H$, $R_1=R_2=CH_3$, $R_3=R_4=H$, n=1, $R_7=C_2H_5$ 50 g of 3,3-dimethylglutaric anhydride are dissolved in 500 ml of absolute ethanol and the mixture is refluxed for 12 hours. The alcohol is evaporated off to dryness under vacuum, 250 ml of toluene are added to the residue and 45 ml of thionyl chloride are then added dropwise at room temperature, with stirring. The mixture is heated at 80° C. for two hours, the solvents are then evaporated off and the residue is distilled at between 115° and 125° C. under 20 mm of mercury to give 58.2 g of the acid chloride ethyl ester of 3,3-dimethylglutaric acid.

The following Examples were prepared by the same procedure:

EXAMPLE 29

Acid chloride ethyl ester of 3-methylglutaric acid

Formula (VIII): $R_5=R_6=H$, $R_1=CH_3$, $R_2=R_3=R_4=H$, n=1, $R_7=C_2H_5$

Oil used as such for the next step.

EXAMPLE 30

Acid chloride ethyl ester of 3,3-diethylglutaric acid

Formula (VIII): $R_5=R_6=H$, $R_1=R_2=C_2H_5$, $R_3=R_4=H$, n=1, $R_7=C_2H_5$

Oil used as such for the next step.

EXAMPLE 31

Acid chloride ethyl ester of 3-methyl-3-ethylglutaric acid

Formula (VIII): $R_5=R_6=H$, $R_1=CH_3$, $R_2=C_2H_5$, $R_3=R_4=H$, n=1, $R_7=C_2H_5$ Oil used as such for the next step.

EXAMPLE 32

Acid chloride ethyl ester of cyclohexane-1,1-diacetic acid

Formula (VIII): $R_5=R_6=H$, $R_1+R_2=CH_2\text{-}CH_2\text{-}CH_2\text{-}CH_2\text{-}CH_2$, $R_3=R_4=H$, n=1, $R_7=C_2H_5$ Oil boiling at 170°-175° C. under 25 mm of mercury.

EXAMPLE 33

Acid chloride ethyl ester of cyclopentane-1,1-diacetic acid

Formula (VIII): $R_5=R_6=H$, $R_1+R_2=CH_2\text{-}CH_2\text{-}CH_2\text{-}CH_2$, $R_3=R_4=H$, n=1, $R_7=C_2H_5$ Oil boiling at 165°-170° C. under 25 mm of mercury.

EXAMPLE 34

Ethyl 4-[1-(4-chlorobenzyl)-5-fluorobenzimidazol-2-yl]-3,3-dimethylbutanoate

Formula (I): $R_1=R_2=CH_3$, $R_3=R_4=H$, n=1, $D=CO_2Et$, A=phenyl, $B=CH_2$, $X_1=5\text{-F}$, $X_2=H$, $X_3=4\text{-Cl}$, $X_4=H$ 10 g of 2-(4-chlorobenzylamino)-5-fluoroaniline, prepared in Example 8, are dissolved in 100 ml of chloroform, stabilized with amylene, and 6 ml of triethylamine. A solution of 8.25 g of the acid chloride ethyl ester of 3,3-dimethylglutaric acid, prepared in Example 28, in 20 ml of chloroform, stabilized with amylene, is added dropwise. The mixture is stirred for two hours at room temperature, the crystals formed are filtered off and the solvents are evaporated off under vacuum. The residue obtained is dissolved in 200 ml of ethanol and 30 ml of concentrated hydrochloric acid and the mixture is refluxed for 10 hours. The solvents are evaporated off to dryness and the residue is taken up with water and then extracted with ethyl acetate. The organic phase is dried and evaporated under vacuum to give 14 g of ethyl 4-[1-(4-chlorobenzyl)-5-fluorobenzimidazol-2-yl]-3,3-dimethylbutanoate in the form of an oil, which is used as such for the next step.

The following Examples were synthesized by the same procedure:

EXAMPLE 35

Ethyl [1-[1-(4-chlorobenzyl)-5-fluorobenzimidazol-2-yl]methylcyclopent-1-yl]acetate Formula (I): $R_1+R_2=CH_2\text{-}CH_2\text{-}CH_2\text{-}CH_2$, $R_3=R_4=H$, n=1, $D=CO_2Et$, A=phenyl, $B=CH_2$, $X_1=5\text{-F}$, $X_2=H$, $X_3=4\text{-Cl}$, $X_4=H$ Oil used as such for the next step.

EXAMPLE 36

Ethyl [1-[1-(4-chlorobenzyl)-5-fluorobenzimidazol-2-yl]methylcyclohex-1-yl]acetate Formula (I): $R_1+R_2=CH_2\text{-}CH_2\text{-}CH_2\text{-}CH_2CH_2$, $R_3=R_4=H$, n=1, $D=CO_2Et$, A=phenyl, $B=CH_2$, $X_1=5\text{-F}$, $X_2=H$, $X_3=4\text{-Cl}$, $X_4=H$

EXAMPLE 37

Ethyl 4-[1-(3,4-dichlorobenzyl)-5-fluorobenzimidazol-2-yl]-3,3-dimethylbutanoate Formula (I): $R_1=R_2=CH_3$, $R_3=R_4=H$, $n=1$, $D=CO_2Et$, $A=$phenyl, $B=CH_2$, $X_1=5$-F, $X_2=H$, $X_3=3$-Cl, $X_4=4$-Cl Oil used as such for the next step.

EXAMPLE 38

Ethyl 4-[1-(4-chlorobenzyl)-5-chlorobenzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=5$-Cl, $X_2=H$, $X_3=4$-Cl, $X_4=H$ Oil used as such for the next step.

EXAMPLE 39

Ethyl 4-[1-(4-chlorobenzyl)-5-methoxybenzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_1=5$-MeO, $X_2=H$, $X_3=4$-Cl, $X_4=H$ Oil used as such for the next step.

EXAMPLE 40

Ethyl 4-(benzimidazol-2-yl)-3,3-dimethylbutanoate

Formula (XI): $B=CH_2$, $R_1=R_2=CH_3$, $R_3=R_4=H$, $n=1$, $R_7=C_2H_5$, $X_1=X_2=H$ A solution of 139.2 g of the acid chloride ethyl ester of 3,3-dimethylglutaric acid, prepared in Example 28, in 125 ml of chloroform, stabilized with amylene, is added dropwise, at a temperature of between 5° C. and 10° C., to a solution of 72.8 g of orthophenylenediamine and 112 ml of triethylamine in 1 l of anhydrous tetrahydrofuran. The mixture is stirred at 0° C. for two hours and then at 50° C. for one hour; the crystals are filtered off and the solvents are evaporated off under vacuum. The residue is taken up in 4.4 l of ethanol and 444 ml of concentrated hydrochloric acid and the mixture is refluxed for 12 hours. The solvents are evaporated off and the residue is taken up with water and then neutralized with a 1 N solution of sodium hydroxide and extracted with ether. The ether phase is dried and then evaporated under vacuum to give 99 g of ethyl 4-(benzimidazol-2-yl)-3,3-dimethylbutanoate in the form of crystals melting at 123° C.

The following Examples were prepared by the same procedure:

EXAMPLE 41

Ethyl 4-(5,6-dichlorobenzimidazol-2-yl)-3,3-dimethylbutanoate

Formula (XI): $B=CH_2$, $R_1=R_2=CH_3$, $R_3=R_4=H$, $n=1$, $R_7=C_2H_5$, $X_1=5$-Cl, $X_2=6$-Cl Crystals melting at 128° C.

EXAMPLE 42

Ethyl 4-(benzimidazol-2-yl)-3-methyl-3-ethylbutanoate

Formula (XI): $B=CH_2$, $R_1=CH_3$, $R_2=C_2H_5$, $R_3=R_4=H$, $n=1$, $R_7=C_2H_5$, $X_1=X_2=H$ Oil used as such for the next step.

EXAMPLE 43

Ethyl 4-(benzimidazol-2-yl)-3,3-diethylbutanoate

Formula (XI): $B=CH_2$, $R_1=R_2=C_2H_5$, $R_3=R_4=H$, $n=1$, $R_7=C_2H_5$, $X_1=X_2=H$ Crystals melting at 81° C.

EXAMPLE 44

Ethyl 4-(benzimidazol-2-yl)-3-methylbutanoate

Formula (XI): $B=CH_2$, $R_1=CH_3$, $R_2=R_3=R_4=H$, $n=1$, $R_7=C_2H_5$, $X_1=X_2=H$ Crystals melting at 105° C.

EXAMPLE 45

Ethyl 4-[1-(4-chlorobenzyl)benzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=H$, $X_2=X_3=H$, $X_4=4$-Cl 9 g of ethyl 4-(benzimidazol-2-yl)-3,3-dimethylbutanoate, prepared in Example 40, are added to a suspension of 21.5 g of 60% sodium hydride in 50 ml of anhydrous dimethylformamide. The mixture is stirred for 1 hour at 50° C., 5.6 g of 4-chlorobenzyl chloride are then added and the solution obtained is heated for 5 hours at 90° C. The solvents are concentrated under vacuum and the residue is taken up with water and then extracted with ether. The ether phase is washed with water and then dried over magnesium sulfate and the ether is evaporated off to dryness to give 12.9 g of ethyl 4-[1-(4-chlorobenzyl)benzimidazol-2-yl]-3,3-dimethylbutanoate in the form of an oil, which is used as such for the next step.

The following Examples were prepared by the same procedure:

EXAMPLE 46

Ethyl 4-[1-(2-fluoro-4-bromobenzyl)benzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=H$, $X_2=H$, $X_3=2$-F, $X_4=4$-Br Oil used as such for the next step.

EXAMPLE 47

Ethyl 4-(1-benzylbenzimidazol-2-yl)3,3-dimethylbutanoate

Formula (I): $R_1=R_2=CH_3$, $R_3=R_4=H$, $n=1$, $D=CO_2Et$, $A=$phenyl, $B=CH_2$, $X_1=X_2=X_3=X_4=H$ Oil used as such for the next step.

EXAMPLE 48

Ethyl 4-[1-(4-methylbenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_1=X_2=X_3=H$, $X_4=$4-Me Oil used as such for the next step.

EXAMPLE 49

Ethyl 4-[1-(4-fluorobenzyl)benzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=X_2=X_3=H$, $X_4=$4-F Oil used as such for the next step.

EXAMPLE 50

Ethyl 4-[1-(4-methoxybenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_3=$4-MeO, $X_1=X_2=X_4=H$ Oil used as such for the next step.

EXAMPLE 51

Ethyl 4-[1-(4-bromobenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_3=$4-Br, $X_1=X_2=X_4=H$ Oil used as such for the next step.

EXAMPLE 52

Ethyl 4-[1-(4-chlorobenzyl)-5,6-dichlorobenzimidazol-2-yl]-3,3-dimethylbutanoate Formula (I): $R_1=R_2=CH_3$, $R_3=R_4=H$, $n=1$, $D=CO_2Et$, $B=CH_2$, $A=$phenyl, $X_1=$5-Cl, $X_2=$6-Cl, $X_3=$4-Cl, $X_4=H$ Oil used as such for the next step.

EXAMPLE 53

Ethyl 4-[1-(3-trifluoromethylbenzyl)benzimidazol-2yl]-3,3-dimethylbutanoate

Formula (I): $R_1=R_2=CH_3$, $R_3=R_4=H$, $n=1$, $D=CO_2Et$, $B=CH_2$, $A=$phenyl, $X_1=H$, $X_2=X_3=H$, $X_4=$3-CF$_3$ Oil used as such for the next step.

EXAMPLE 54

Ethyl 4-[1-(4-chlorobenzyl)benzimidazol-2-yl]-3-methyl-3-ethylbutanoate

Formula (I): $R_1=CH_3$, $R_2=C_2H_5$, $R_3=R_4=H$, $n=1$, $D=CO_2Et$, $B=CH_2$, $A=$phenyl, $X_1=H$, $X_2=X_3=H$, $X_4=$4-Cl Oil used as such for the next step.

EXAMPLE 55

Ethyl 4-[1-(4-chlorobenzyl)benzimidazol-2-yl]-3,3-diethylbutanoate

Formula (I): $R_1=R_2=C_2H_5$, $R_3=R_4=H$, $n=1$, $D=CO_2Et$, $B=CH_2$, $A=$phenyl, $X_1=H$, $X_2=X_3H$, $X_4=$4-Cl, Oil used as such for the next step.

EXAMPLE 55

Ethyl 4-[1-(4-chlorobenzyl)benzimidazol-2-yl]-3,3-diethylbutanoate

Formula (I): $R_1=R_2=C_2H_5$, $R_3=R_4=H$, $n=1$, $D=CO_2Et$, $B=CH_2$, $A=$phenyl, $X_1=H$, $X_2=H$, $X_3=$4-Cl, $X_4=H$ Oil used as such for the next step.

EXAMPLE 56

Ethyl 4-[1-(4-chlorobenzyl)benzimidazol-2-yl]-3-methylbutanoate

Formula (I): $R_1=CH_3$, $R_2=H$, $R_3=R_4=H$, $n=1$, $D=CO_2Et$, $B=CH_2$, $A=$phenyl, $X_1=X_2=X_3=H$, $X_4=$4-Cl Oil used as such for the next step.

EXAMPLE 57

Ethyl 4-[1-(naphth-2-ylmethyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_3+X_4$ form a phenyl ring in the 3,4-position, $X_1=X_2=H$ Oil used as such for the next step.

EXAMPLE 58

4-(1-Benzylbenzimidazol-2-yl)-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=X_4=H$ 9 g of ethyl 4-(1-benzylbenzimidazol-2-yl)-3,3-dimethylbutanoate, prepared in Example 47, are dissolved in a mixture composed of 90 ml of concentrated hydrochloric acid, 270 ml of water and 250 ml of acetic acid. The mixture is refluxed for 4 hours and the solvents are concentrated under vacuum. The residue is taken up with a 1N solution of sodium hydroxide and the resulting mixture is washed with ether; the aqueous phase is acidified by having sulfur dioxide bubbled through it until the pH is 5–6, and the crystals formed are filtered off and washed with water and isopropyl ether to give 5.3 g of 4-(1-benzylbenzimidazol-2-yl)-3,3-dimethylbutanoic acid in the form of crystals melting at 160°−1° C.

The following compounds were prepared by the same procedure:

EXAMPLE 59

5-[1-(4-Chlorobenzyl)-5-fluorobenzimidazol-2-yl]mercaptopentanoic acid

Formula (I): $R_1=R_2=R_3=R_4=H$, $n=3$, $D=CO_2H$, $B=S$, $A=$phenyl, $X_1=$5-F, $X_2=X_3=H$, $X_4=$4-Cl Crystals melting at 184°–186° C.

EXAMPLE 60

4-[1-(2-Fluoro-4-bromobenzyl)-5-chloroimidazo[4,5-b]-pyridin-2-yl]mercaptobutanoic acid Formula (I): $R_1=R_2=R_3=R_4=H$, $n=2$, $D=CO_2H$, $B=S$, $A=$phenyl, $X_1=5$-Cl, $X_2=H$, $X_3=2$-F, $X_4=4$-Br Crystals melting at 156°–158° C.

EXAMPLE 61

2-[1-(4-Chlorobenzyl)-5-chloroimidazo[4,5-b]pyridin-2-yl]mercapto-2-methylpropanoic acid Formula (I): $R_1=R_2=CH_3$, $n=0$, $D=CO_2H$, $B=S$, $A=$phenyl, $X_1=5$-Cl, $X_2=H$, $X_3=4$-Cl, $X_4=H$ Crystals melting at 188°–189° C.

EXAMPLE 62

4-[1-(4-Chlorobenzyl)imidazo[4,5-b]pyridin-2-yl]mercaptobutanoic acid

Formula (I): $R_1=R_2=R_3=R_4=H$, $n=2$, $D=CO_2H$, $B=S$, $A=$phenyl, $X_1=X_2=H$, $X_3=4$-Cl, $X_4=H$ Crystals melting at 121°–122° C.

EXAMPLE 63

4-[1-(4-Chlorobenzyl)benzimidazol-2-yl]mercaptobutanoic acid

Formula (I): $R_1=R_2=R_3=R_4=H$, $n=2$, $D=CO_2H$, $B=S$, $A=$phenyl, $X_1=X_2=X_3=H$, $X_4=4$-Cl Crystals melting at 187°–190° C.

EXAMPLE 64

4-[1-(2,4-Dichlorobenzyl)benzimidazol-2-yl]mercaptobutanoic acid

Formula (I): $R_1=R_2=R_3=R_4=H$, $n=2$, $D=CO_2H$, $B=S$, $A=$phenyl, $X_1=X_2=H$, $X_3=2$-Cl, $X_4=4$-Cl Crystals melting at 117°–120° C.

EXAMPLE 65

4-[1-(4-Chlorobenzyl)-5-fluorobenzimidazol-2-yl]mercaptobutanoic acid

Formula (I): $R_1=R_2=R_3=R_4=H$, $n=2$, $D=CO_2H$, $B=S$, $A=$phenyl, $X_1=5$-F, $X_2=X_3=H$, $X_4=4$-Cl Crystals melting at 176°–178° C.

EXAMPLE 66

4-[1-(4-Methylbenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=4$-Me Crystals melting at 147°–148° C.

EXAMPLE 67

4-[1-(4-Fluorobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=4$-F Crystals melting at 180°–181° C.

EXAMPLE 68

4-[1-(4-Methoxybenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=4$-MeO Crystals melting at 149°–150° C.

EXAMPLE 69

4-[1-(4-Bromobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=4$-Br Crystals melting at 171°–172° C.

EXAMPLE 70

4-[1-(4-Chlorobenzyl)-5,6-dichlorobenzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=5$-Cl, $X_2=6$-Cl, $X_3=H$, $X_4=4$-Cl Crystals melting at 197°–199° C.

EXAMPLE 71

4-[1-(3-Trifluoromethylbenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=3$-CF$_3$ Crystals melting at 163°–164° C.

EXAMPLE 72

[1-[1-(4-Chlorobenzyl)-5-fluorobenzimidazol-2-yl]methylcyclopent-1-yl]acetic acid Formula (I): $R_1+R_2=CH_2CH_2CH_2CH_2$, $R_3=R_4=H$, $n=1$, $D=CO_2H$, $B=CH_2$, $A=$phenyl, $X_1=5$-F, $X_2=X_3=H$, $X_4=4$-Cl Crystals melting at 164°–165° C.

EXAMPLE 73

[1-[1-(4-Chlorobenzyl)-5-fluorobenzimidazol-2-yl]methylcyclohex-1-yl]acetic acid Formula (I): $R_1+R_2=CH_2CH_2CH_2CH_2CH_2$, $R_3=R_4=H$, $n=1$, $D=CO_2H$, $B=CH_2$, $A=$phenyl, $X_1=5$-F, $X_2=X_3=H$, $X_4=4$-Cl Crystals melting at 182°–184° C.

EXAMPLE 74

4-[1-(4-Chlorobenzyl)-5-fluorobenzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=5$-F, $X_2=X_3=H$, $X_4=4$-Cl Crystals melting at 164°–165° C.

EXAMPLE 75

4-[1-(4-Chlorobenzyl)benzimidazol-2-yl]-3-methyl-3-ethylbutanoic acid

Formula (I): $R_1=C_2H_5$, $R_2=CH_3$, $R_3=R_4=H$, $n=1$, $D=CO_2H$, $B=CH_2$, $A=$phenyl, $X_1=X_2=X_3=H$, $X_4=4$-Cl Crystals melting at 120°–123° C.

EXAMPLE 76

4-[1-(2-Fluoro-4-bromobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=H$, $X_3=2$-F, $X_4=4$-Br Crystals melting at 147°-148° C.

EXAMPLE 77

4-[1-(4-Chlorobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=4$-Cl Crystals melting at 170°-171° C.

EXAMPLE 78

4-[1-(4-Chlorobenzyl)-5-methoxybenzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=5$-MeO, $X_2=X_3=H$, $X_4=4$-Cl Crystals melting at 174°-176° C.

EXAMPLE 79

4-[1-(4-Chlorobenzyl)-5-chlorobenzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=5$-Cl, $X_2=X_3=H$, $X_4=4$-Cl Crystals melting at 205°-207° C.

EXAMPLE 80

4-[1-(3,4-Dichlorobenzyl)-5-fluorobenzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=5$-F, $X_2=H$, $X_3=3$-Cl, $X_4=4$-Cl Crystals melting at 177°-180° C.

EXAMPLE 81

4-[1-(4-Nitrobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=H$, $X_4=4$-$NO_2$ Crystals melting at 192°-194° C.

EXAMPLE 82

4-[1-(4-Chlorobenzyl)benzimidazol-2-yl]-3,3-diethylbutanoic acid

Formula (I): $R_1=R_2=C_2H_5$, $R_3=R_4=H$, $n=1$, $D=CO_2H$, $B=CH_2$, $A=$phenyl, $X_1=X_2=X_3=H$, $X_4=4$-Cl Crystals melting at 139°-140° C.

EXAMPLE 83

4-[1-(4-Chlorobenzyl)benzimidazol-2-yl]-3-methylbutanoic acid

Formula (I): $R_1=H$, $R_2=CH_3$, $R_3=R_4=H$, $n=1$, $D=CO_2H$, $B=CH_2$, $A=$phenyl, $X_1=X_2=X_3=H$, $X_4=4$-Cl Crystals melting at 201°-202° C.

EXAMPLE 84

4-[1-(Naphth-2-ylmethyl)benzimidazol-2-yl]-3,3-dimethylbutanoic acid

Formula (I): $A=$phenyl, $B=CH_2$, $D=CO_2H$, $R_1=R_2=CH_3$, $R_3=R_4=H$, $n=1$, $X_1=X_2=H$, $X_3+X_4$ form a phenyl ring in the 3,4-position Crystals melting at 147°-149° C.

EXAMPLE 85

4-[1-(4-Chlorobenzyl)benzimidazol-2-yl]-3,3-dimethylbutanamide

Formula (I): $R_1=R_2=CH_3$, $R_3=R_4=H$, $n=1$, $B=CH_2$, $D=CONH_2$, $A=$phenyl, $X_3=4$-Cl, $X_1=X_2=X_4=H$ 11.7 g of 4-[1-(4-chlorobenzyl)benzimidazol-2-yl]-3,3-dimethylbutanoic acid, prepared in Example 77, are added to 100 ml of anhydrous toluene and 3 ml of thionyl chloride. The mixture is heated at 80° C. for 4 hours and the solvents are evaporated off under vacuum. The residue is taken up in 50 ml of chloroform, stabilized with amylene, and added dropwise to 50 ml of 28% ammonium hydroxide. When the addition is complete, the mixture is stirred at room temperature for 1 hour 30 minutes and then decanted. The organic phase is dried over magnesium sulfate and the solvent is evaporated off to dryness under vacuum. The residue crystallizes from isopropyl ether and is recrystallized from acetonitrile to give 5.1 g of 4-[1-(4-chlorobenzyl)benzimidazol-2-yl]-3,3-dimethylbutanamide in the form of crystals melting at 163°-165° C.

EXAMPLE 86

4-[1-(4-Chlorobenzyl)benzimidazol-2-yl]-3,3-dimethylbutyronitrile

Formula (I): $R_1=R_2=CH_3$, $R_3=R_4=H$, $n=1$, $B=CH_2$, $D=CN$, $A=$phenyl, $X_3=4$-Cl, $X_1=X_2=X_4=H$ 2.7 g of 4-[1-(4-chlorobenzyl)benzimidazol-2-yl]-3,3-dimethylbutanamide are dissolved in 50 ml of chloroform. 2.3 ml of phosphorus oxychloride are added and the mixture is refluxed for 5 hours. After cooling, the solvents are evaporated off under vacuum and the residue is taken up with water and extracted with ethyl acetate. The organic phase is dried over magnesium sulfate and evaporated to dryness under vacuum to give an oil which crystallizes from ether. The crystals are filtered off, washed with ether and then dried to give 2.5 g of 4-[1-(4-chlorobenzyl)benzimidazol-2-yl]-3,3-dimethylbutyronitrile in the form of crystals melting at 110° C.

EXAMPLE 87

4-[1-(4-Hydroxybenzyl)benzimidazol-2-yl]-3,3-dimethylbutanoic acid

Formula (I): $R_1=R_2=CH_3$, $R_3=R_4=H$, $n=1$, $B=CH_2$, $D=CO_2H$, $A=$phenyl, $X_4=4$-OH, $X_1=X_2=X_3=H$ 2.7 g of 4-[1-(4-methoxybenzyl)benzimidazol-2-yl]-3,3-dimethylbutanoic acid, prepared in Example 68, are dissolved in 40 ml of acetic acid and 40 ml of 48% hydrobromic acid. The mixture is refluxed for 3 hours and the solvents are evaporated off under vacuum. The residue is taken up with a 1N solution of sodium hydroxide so as to adjust the pH to 9-10, and the resulting aqueous phase is washed with ether and then acidified with sulfur dioxide to pH 5.5. The crystals obtained are filtered off, washed with water and then with ether and then chromatographed on silica gel in a 9:1 chloroform-/methanol eluent to give 0.4 g of 4-[1-(4-hydroxybenzyl)benzimidazol-2-yl]-3,3-dimethylbutanoic acid in the form of crystals melting at 215°–216° C.

EXAMPLE 88

Acid chloride ethyl ester of trans-cyclobutane-1,2-dicarboxylic acid

Formula (VIII): $R_1+R_5=CH_2-CH_2$, $R_2=R_6=H$, $R_7=C_2H_5$, n=0

14.2 g of ethyl trans-cyclobutane-1,2-dicarboxylate are dissolved in 100 ml of ethanol, and 2.8 g of sodium hydroxide pellets are added together with 30 ml of water. The mixture is refluxed for 1 hour and the solvents are evaporated off under vacuum. The residue is taken up with water and washed with ether. The aqueous phase is acidified with dilute hydrochloric acid and extracted with ether. The ether phase is dried over magnesium sulfate and evaporated under vacuum to give 7.5 g of the monoethyl ester of trans-cyclobutane-1,2-dicarboxylic acid. 6 ml of thionyl chloride and 50 ml of toluene are added to these 7.5 g and the mixture is refluxed for two hours. The solvents are evaporated off to dryness to give 9 g of the acid chloride ethyl ester of trans-cyclobutane-1,2-dicarboxylic acid in the form of an oil, which is used as such for the next step.

EXAMPLE 89

Ethyl trans-2-[1-(4-chlorobenzyl)-5-fluorobenzimidazol-2-yl]cyclobutane-1-carboxylate Formula (I): B=

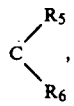

$R_1+R_5=CH_2CH_2$, $R_2=R_6=H$, n=0, D=CO$_2$Et, A=phenyl, $X_1$=5-F, $X_2$=H, $X_3$=4-Cl, $X_4$=H Prepared by the procedure of Example 34.
Oil used as such for the next step.

EXAMPLE 90

Trans-2-[1-(4-chlorobenzyl)-5-fluorobenzimidazol-2-yl]-cyclobutane-1-carboxylic acid Formula (I): B=

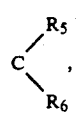

$R_1+R_5=CH_2CH_2$, $R_2=R_6=H$, n=0, D=CO$_2$H, A=phenyl, $X_1$=5-F, $X_2$=H, $X_3$=4-Cl, $X_4$=H Prepared by the procedure of Example 58.
Crystals melting at 173°–175° C.

EXAMPLE 91

Ethyl 4-[1-(4-chlorophenylmethyl)-5-chloroimidazo[4,5-b]pyridin-2-yl]-3,3-dimethylbutanoate Formula (I): $R_1=R_2=CH_3$, $R_3=R_4=H$, n=1, D=COOEt, A=pyridin-2-yl, B=CH$_2$, $X_1$=5-Cl, $X_2=X_3$=H, $X_4$=4-Cl If the procedure of Example 40 is followed, except that 2-(4-chlorophenylmethylamino)-3-amino-5-chloropyridine, prepared in Example 14, is used as the starting material, ethyl 4-[1-(4-chlorophenylmethyl)-5-chloroimidazo[4,5-b]pyridin-2-yl]-3,3-dimethylbutanoate is obtained in the form of an oil, which is used as such for the next step.

EXAMPLE 92

4-[1-(4-Chlorophenylmethyl)-5-chloroimidazo[4,5-b]pyridin-2-yl]-3,3-dimethylbutanoic acid Formula (I): $R_1=R_2=CH_3$, $R_3=R_4=H$, n=1, D=COOH, A=pyridin-2-yl, B=CH$_2$, $X_1$=5-Cl, $X_2=X_3$=H, $X_4$=4-Cl If the procedure of Example 58 is followed, except that ethyl 4-[1-(4-chlorophenylmethyl)-5-chloroimidazo[4,5-b]pyridin-2-yl]-3,3-dimethylbutanoate, prepared in Example 91, is used as the starting material, 4-[1-(4-chlorophenylmethyl)-5-chloroimidazo[4,5-b]pyridin-2-yl]-3,3-dimethylbutanoic acid is obtained in the form of crystals melting at 120°–122° C.

TABLE

| Example 58 | ![structure] | UP 116-52 |
| Example 59 | ![structure] | UP 116-11 |
| Example 60 | ![structure] | UP 116-17 |
| Example 61 | ![structure] | UP 116-21 |

TABLE-continued

| Example | Structure | Code |
|---|---|---|
| Example 62 | imidazopyridine, N-(4-chlorobenzyl), 2-S(CH$_2$)$_3$-CO$_2$H | UP 116-13 |
| Example 63 | benzimidazole, N-(4-chlorobenzyl), 2-S(CH$_2$)$_3$-CO$_2$H | UP 116-16 |
| Example 64 | benzimidazole, N-(2,4-dichlorobenzyl), 2-S(CH$_2$)$_3$-CO$_2$H | UP 116-18 |
| Example 65 | 5-F-benzimidazole, N-(4-chlorobenzyl), 2-S(CH$_2$)$_3$-CO$_2$H | UP 116-1 |
| Example 66 | benzimidazole, N-(4-methylbenzyl), 2-C(CH$_3$)$_2$CH$_2$-CO$_2$H | UP 116-57 |
| Example 67 | benzimidazole, N-(4-fluorobenzyl), 2-C(CH$_3$)$_2$CH$_2$-CO$_2$H | UP 116-56 |
| Example 68 | benzimidazole, N-(4-methoxybenzyl), 2-C(CH$_3$)$_2$CH$_2$-CO$_2$H | UP 116-55 |
| Example 69 | benzimidazole, N-(4-bromobenzyl), 2-C(CH$_3$)$_2$CH$_2$-CO$_2$H | UP 116-59 |
| Example 70 | 5,6-dichlorobenzimidazole, N-(4-chlorobenzyl), 2-C(CH$_3$)$_2$CH$_2$-CO$_2$H | UP 116-63 |
| Example 71 | benzimidazole, N-(3-trifluoromethylbenzyl), 2-C(CH$_3$)$_2$CH$_2$-CO$_2$H | UP 116-67 |
| Example 72 | 5-F-benzimidazole, N-(4-chlorobenzyl), 2-(1-cyclopentyl)CH$_2$-CO$_2$H | UP 116-53 |
| Example 73 | 5-F-benzimidazole, N-(4-chlorobenzyl), 2-(1-cyclohexyl)CH$_2$-CO$_2$H | UP 116-54 |
| Example 74 | 5-F-benzimidazole, N-(4-chlorobenzyl), 2-C(CH$_3$)$_2$CH$_2$-CO$_2$H | UP 116-47 |
| Example 75 | benzimidazole, N-(4-chlorobenzyl), 2-C(CH$_3$)(C$_2$H$_5$)CH$_2$-CO$_2$H | UP 116-65 |

TABLE-continued
| Example 76 | 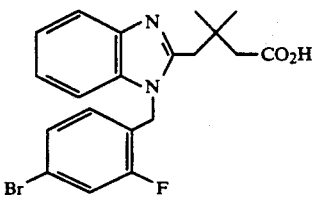 | UP 116-51 |
| Example 77 | 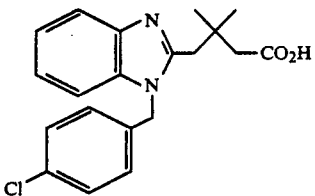 | UP 116-58 |
| Example 78 | 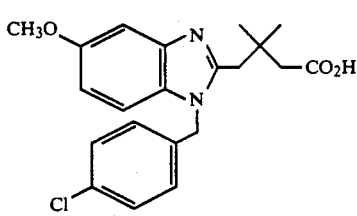 | UP 116-64 |
| Example 79 | 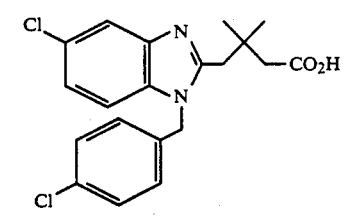 | UP 116-60 |
| Example 80 | 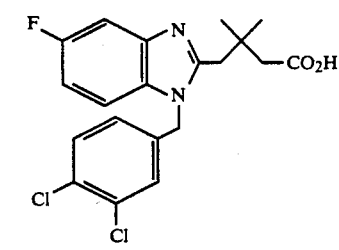 | UP 116-62 |
| Example 81 | 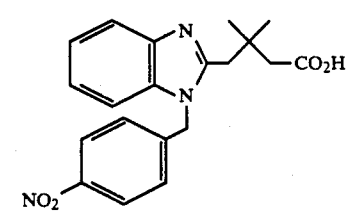 | UP 116-66 |
| Example 82 | 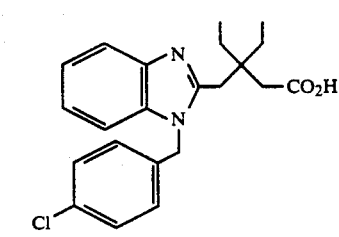 | UP 116-68 |
TABLE-continued
| Example 83 | 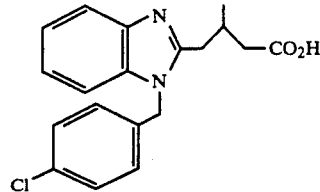 | UP 116-70 |
| Example 84 | 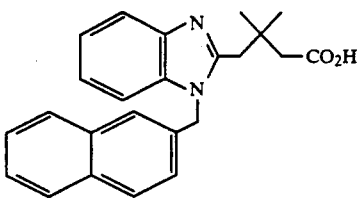 | UP 116-71 |
| Example 85 | 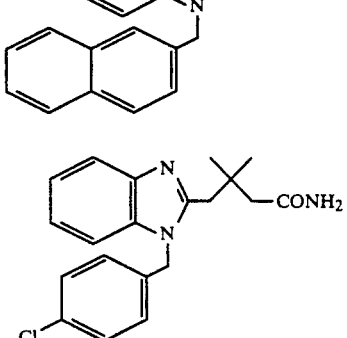 | UP 116-72 |
| Example 86 | 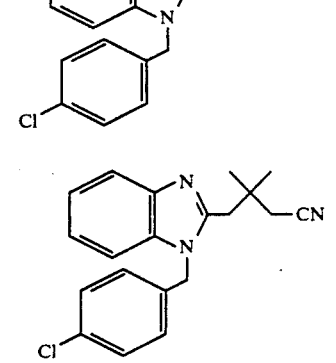 | UP 116-73 |
| Example 87 | 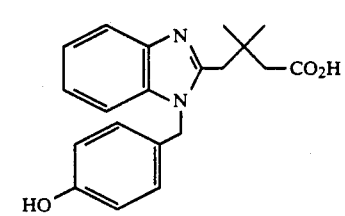 | UP 116-61 |
| Example 90 | 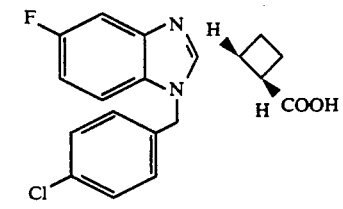 | UP 116-74 |
| Example 92 | 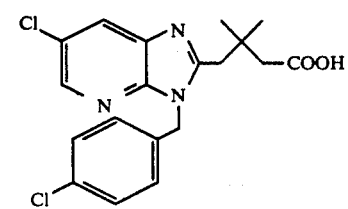 | UP 116-77 |
PHARMACOLOGY
Principle
The affinity of the products of the Examples described for thromboxane $A_2$ receptors is evaluated by the technique of displacing a radioligand specifically bound to the $TXA_2$ receptors of human platelets.

Technique

Human platelets incubate in the presence of a single concentration of [$^{125}$I]PTA-OH (9,11-dimethylmethano-11,12-methano-16-(3[$^{125}$I]iodo-4-hydroxyphenyl)-13,14-dihydro-13-aza-15α-w-tetranor-$TXA_2$), $TXA_2$ receptor antagonist ($PGH_2$) and two concentrations of competing agents ($10^{-5}M$, $10^{-7}M$) for 30 min at 37° C.

The reaction is completed by the addition of a buffer, followed by rapid filtration through glasspaper filters.

The non-specific binding is determined in the presence of U 46619 (9,11-dideoxy-11α,9α-epoxymethanoprostaglandin $F_2α$; mimetic thromboxane $A_2$).

Results

The results are expressed, for the doses tested, as the percentage displacement of the radioligand specifically bound to the $TXA_2$ receptors of human platelets.

Toxicology

Preliminary toxicity studies were able to show that the 50% lethal doses determined after oral administration to rats were greater than 300 mg/kg, representing an advantageous therapeutic index.

Conclusion

In conclusion, the molecules described in the present patent application, or their non-toxic addition salts, exhibit a substantial affinity for $TXA_2$ receptors and can be advantageously and profitably used in the treatment of the following pathological conditions:

myocardial infarction, angina pectoris, stroke, migraine, cerebral hemorrhage, atherosclerosis, pulmonary embolism, bronchial asthma, bronchitis, pneumonia, circulatory shock of various origins (hemorrhage, septicemia, heart failure, trauma, acute pancreatitis, burn, bacterial origin), nephritis, graft rejection and cancerous metastases, by oral administration in the form of tablets or gelatin capsules containing from 1 to 200 mg of active ingredient, or by parenteral administration in the form of injectable preparations containing from 0.01 to 10 mg of active ingredient, preferably in several dosage units (2 to 4) or administrations per day.

|  | % displacement | |
|---------|-------|-------|
| Example | 1E-7 M | 1E-5 M |
| 58 | 13 | 95 |
| 59 | 28 | 100 |
| 60 | 24 | 60 |
| 61 | 30 | 100 |
| 62 | 27 | 64 |
| 63 | 37 | 97 |
| 64 | 34 | 97 |
| 65 | 8 | 93 |
| 66 | 52 | 100 |
| 67 | 66 | 100 |
| 68 | 89 | 100 |
| 69 | 86 | 96 |
| 70 | 14 | 100 |
| 71 | 50 | 100 |
| 72 | 71 | 100 |
| 73 | 0 | 98 |
| 74 | 94 | 100 |
| 75 | 58 | 100 |
| 76 | 88 | 99 |
| 77 | 85 | 100 |
| 78 | 44 | 100 |

-continued

|  | % displacement | |
|---------|-------|-------|
| Example | 1E-7 M | 1E-5 M |
| 79 | 74 | 99 |
| 80 | 89 | 92 |
| 81 | 82 | 100 |
| 82 | 37 | 97 |
| 83 | | |
| 84 | | |
| 85 | | |
| 86 | | |
| 87 | 50 | 96 |

What is claimed is:

1. A benzimidazole derivative of formula (I):

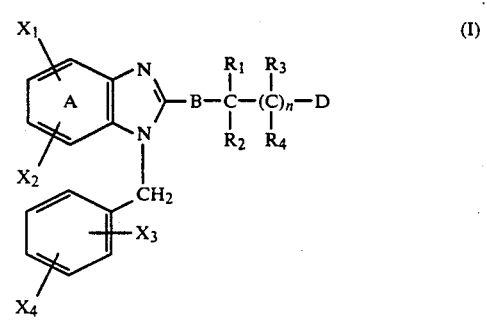

in which:

A is an aromatic ring;

$X_1$, $X_2$, $X_3$ and $X_4$ are independently a hydrogen atom, a halogen atom, a lower alkyl radical, an alkoxy radical, an alkylthio radical, a sulfone group, a sulfoxide group, a trifluoromethyl group, a hydroxyl group, a nitro group, a methylene alcohol radical or a group COOR', in which R' is a hydrogen or a lower alkyl; $X_3$ and $X_4$ can also form a naphthalene with the phenyl;

B is $CR_5R_6$, $R_5$ and $R_6$ being a hydrogen atom or a lower alkyl radical, or the sulfur atom;

$R_1$, $R_2$, $R_3$ and $R_4$ are independently a hydrogen atom or a lower alkyl radical; $CR_1R_2$ or $CR_3R_4$ can form with B, when the latter is $CR_5R_6$, a cycloalkyl or a cycloalkylene having 3 to 7 carbon atoms; $R_1R_2$ and $R_3R_4$ can also form a ring having 3 to 6 carbon atoms;

n is an integer from 1 to 4 and can be 0 if $R_1$ and $R_2$ are other than hydrogen; and D is a chemical group which is: $COOR_7$, $R_7$ being the hydrogen atom or a lower alkyl, $CONH-R_8$, $R_8$ being the hydrogen atom or a lower alkyl, CN,

$R_9$ being the hydrogen atom or a lower alkyl, or $NHSO_2CF_3$, or a pharmaceutically acceptable addition salt thereof.

2. A derivative according to claim 1, wherein A is a phenyl ring.

3. A derivative according to claim 1, wherein $X_1$ is the fluorine atom.

4. A derivative according to claim 1, wherein $X_1$ is the chlorine atom.

5. A derivative according to claim 1, wherein $X_3$ is the chlorine atom.

6. A derivative according to claim 1, wherein $X_3$ is the methoxy group.

7. A derivative according to claim 1, wherein D is an acid group.

8. A derivative according to claim 1, wherein B is a methylene group, $R_1$ and $R_2$ are each a methyl, $R_3$ and $R_4$ are hydrogen and n is equal to 1.

9. A derivative according to claim 1, wherein B is the sulfur atom.

10. A derivative according to claim 1, wherein $CR_1R_2$ is a cyclopentane.

11. A derivative according to claim 1, which is selected from the group consisting of:

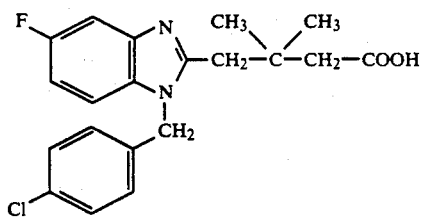

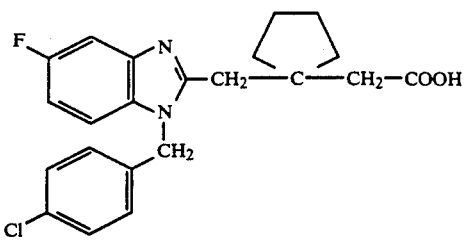

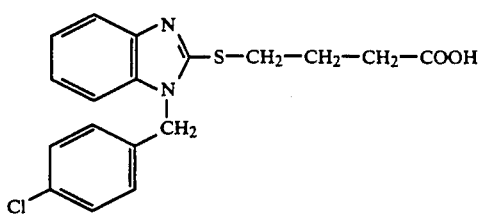

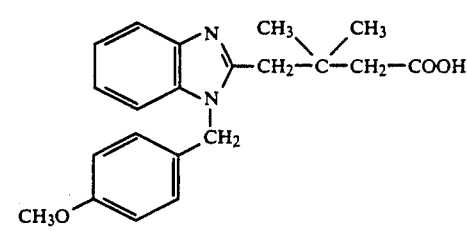

12. A pharmaceutical composition which comprises a pharmaceutically effective amount of a compound of formula (I) as defined in claim 1, or one of its pharmaceutically acceptable addition salts, incorporated in a pharmaceutically acceptable excipient, vehicle or carrier.

13. A pharmaceutical composition which contains, as the active principal, an effective thromboxane receptor antagonist amount of a compound of formula (I) as defined in claim 1, or one of its pharmaceutically acceptable addition salts, and at least one pharmaceutically acceptable carrier.

* * * * *